(12) United States Patent
Latino et al.

(10) Patent No.: US 8,828,126 B2
(45) Date of Patent: Sep. 9, 2014

(54) REMOVABLE FINAL SCRUBBER TUBE

(75) Inventors: Octavio Ramon Latino, Berrian Springs, MI (US); Lloyd Andrew Allen, St. Joseph, MI (US)

(73) Assignee: Leco Corporation, St. Joseph, MI (US)

( * ) Notice: Subject to any disclaimer, the term of this patent is extended or adjusted under 35 U.S.C. 154(b) by 347 days.

(21) Appl. No.: 13/357,894

(22) Filed: Jan. 25, 2012

(65) Prior Publication Data

US 2012/0198690 A1    Aug. 9, 2012

Related U.S. Application Data

(60) Provisional application No. 61/439,605, filed on Feb. 4, 2011.

(51) Int. Cl.
     *B01D 46/00*      (2006.01)
     *G01N 1/40*      (2006.01)

(52) U.S. Cl.
     CPC ...... *G01N 1/4022* (2013.01); *G01N 2001/4066* (2013.01)
     USPC ............. 96/109; 96/147; 96/417; 55/312; 55/410; 55/418; 55/478; 55/480

(58) Field of Classification Search
     CPC .................................................. G01N 1/4022
     USPC ........... 96/108–154, 309, 312, 314, 417–423; 55/480
     See application file for complete search history.

(56) References Cited

U.S. PATENT DOCUMENTS

| | | | | |
|---|---|---|---|---|
| 4,631,073 A | * | 12/1986 | Null et al. | 95/1 |
| 4,872,439 A | * | 10/1989 | Sonoda et al. | 123/519 |
| 4,904,382 A | * | 2/1990 | Thomsen | 210/236 |
| 5,108,598 A | * | 4/1992 | Posner | 210/232 |
| 5,558,688 A | * | 9/1996 | Cowan et al. | 55/312 |
| 5,572,760 A | * | 11/1996 | Patun | 15/21.1 |
| 5,591,332 A | * | 1/1997 | Reid et al. | 210/235 |
| 5,651,887 A | * | 7/1997 | Posner et al. | 210/232 |
| 5,882,384 A | * | 3/1999 | Tom et al. | 96/111 |
| 5,910,165 A | * | 6/1999 | Haramoto et al. | 62/474 |

(Continued)

FOREIGN PATENT DOCUMENTS

EP            606960 A1 *    7/1994            B01D 46/00

OTHER PUBLICATIONS

Pamex, Door Hardwares, Pamex Inc., Dec. 5, 2010, all pages. Product for sale.*

*Primary Examiner* — Duane Smith
*Assistant Examiner* — Britanny Precht
(74) *Attorney, Agent, or Firm* — Price Heneveld LLP

(57) ABSTRACT

A final scrubber in the inert carrier gas flow path of an elemental analyzer includes a manifold with valves for selectively bypassing a quick disconnect final scrubber housing that includes a filter tube and sealed gas fittings. The housing includes alignment members and a latch for positioning and locking the housing onto and in sealed engagement with the instrument's manifold. A switch detects the presence of the housing, and a control circuit controls valves to direct the inert gas flow though the filter tube or bypass the filter tube when the housing is removed. With this system, the final scrubber can be removed and replaced quickly without the use of tools while the carrier gas continues to flow though the furnace without interruption. Also, the valves can be closed to allow for segmented leak detection of the instruments gas flow path.

11 Claims, 18 Drawing Sheets

(56) References Cited

U.S. PATENT DOCUMENTS

| | | | |
|---|---|---|---|
| 5,925,245 A * | 7/1999 | Bradford et al. | 210/232 |
| 6,027,644 A * | 2/2000 | Magnusson et al. | 210/235 |
| 6,051,144 A * | 4/2000 | Clack et al. | 210/739 |
| 6,347,789 B1 * | 2/2002 | Rock | 261/79.1 |
| 6,383,243 B1 * | 5/2002 | Yoder | 55/385.3 |
| 6,458,269 B1 * | 10/2002 | Bassett et al. | 210/119 |
| 6,652,749 B2 * | 11/2003 | Stankowski et al. | 210/232 |
| 6,896,713 B1 * | 5/2005 | Eckerbom et al. | 55/421 |
| 6,918,952 B2 * | 7/2005 | van der Maas | 96/117.5 |
| 6,926,826 B2 * | 8/2005 | Reid | 210/232 |
| 7,378,017 B2 * | 5/2008 | Stankowski et al. | 210/232 |
| 7,399,346 B2 * | 7/2008 | van der Maas | 96/117.5 |
| 7,413,668 B2 * | 8/2008 | Reid | 210/767 |
| 7,608,136 B2 * | 10/2009 | van der Maas | 96/117.5 |
| 7,873,093 B2 * | 1/2011 | van der Maas | 372/59 |
| 7,954,490 B2 * | 6/2011 | Jagger et al. | 128/201.25 |
| 7,964,024 B2 * | 6/2011 | Chen et al. | 95/139 |
| 7,972,418 B2 * | 7/2011 | Hilberer | 95/117 |
| 2002/0089072 A1 * | 7/2002 | Rock | 261/79.1 |
| 2003/0110948 A1 * | 6/2003 | Gaita et al. | 96/108 |
| 2003/0164091 A1 * | 9/2003 | Hill et al. | 95/90 |
| 2003/0168389 A1 * | 9/2003 | Astle et al. | 210/85 |
| 2004/0231517 A1 * | 11/2004 | van der Maas | 96/117.5 |
| 2009/0056720 A1 * | 3/2009 | Chen et al. | 128/205.28 |
| 2009/0065007 A1 * | 3/2009 | Wilkinson et al. | 128/205.27 |
| 2009/0293726 A1 * | 12/2009 | Ammermann et al. | 96/113 |

* cited by examiner

REMOVABLE FINAL SCRUBBER TUBE

CROSS-REFERENCE TO RELATED APPLICATIONS

This application claims priority under 35 U.S.C. §119(e) and the benefit of U.S. Provisional Application No. 61/439,605 entitled REMOVABLE FINISH SCRUBBER TUBE, filed on Feb. 4, 2011, by Octavio Ramon Latino, et al., the entire disclosure of which is incorporated herein by reference.

BACKGROUND OF THE INVENTION

The present invention relates to inert gas fusion analyzers and particularly to an improved system for the replacement of the final scrubber for the inert carrier gas.

In existing gas fusion analyzers, such as Model No. TCH-600 available from Leco Corporation of St. Joseph, Mich., an inert gas, such as helium, is used as a carrier to sweep the byproducts of fusion of a sample in the furnace to the detectors of the analyzer. The carrier gas must be substantially free of contaminates and impurities which would interfere with accurate detection of the desired elements. Thus, oxygen or moisture, for example, must be removed from the carrier gas stream before it enters the furnace. Contaminates are removed by a finish or final scrubber in the carrier gas stream which is typically located in close proximity to the carrier gas inlet to the combustion furnace.

Prior art systems required the use of tools and a somewhat complicated procedure to remove and replace the final scrubber.

SUMMARY OF THE INVENTION

A system for changing a filter element in an analyzer includes a fluid flow path includes a manifold with input and output fluid fittings and at least one valve coupled to one of the input and output fittings. A housing for a filter element includes fluid fittings which align with and couple to associated ones of input and output fluid fittings of the manifold. The housing includes a valve controlling actuator, such that, when the housing is removed from the manifold for the replacement of a filter mounted to the housing, the valve shuts off the flow path to the input and output fittings. The housing includes mechanical valves which seal the housing when removed from the manifold. The system of the present invention, thus, includes a manifold with valves for selectively bypassing a quick disconnect final scrubber housing that includes a filter tube and sealed gas fittings. In one embodiment, the housing includes alignment members and a latch for positioning and locking the housing onto and in sealed engagement with the instrument's manifold. A switch detects the presence of the housing, and a control circuit controls valves to direct the inert gas flow either though the filter tube or bypass the filter tube when the housing is removed. With this system, the final scrubber can be removed and replaced quickly without the use of tools while the carrier gas continues to flow though the furnace without interruption of the purging gas flow path through the instruments furnace. Also, the valves can be closed to allow for segmented leak detection of the instruments gas flow path.

These and other features, objects and advantages of the present invention will become apparent upon reading the following description thereof together with reference to the accompanying drawings.

DETAILED DESCRIPTION OF THE PREFERRED EMBODIMENT

Figures 13A, 13B:
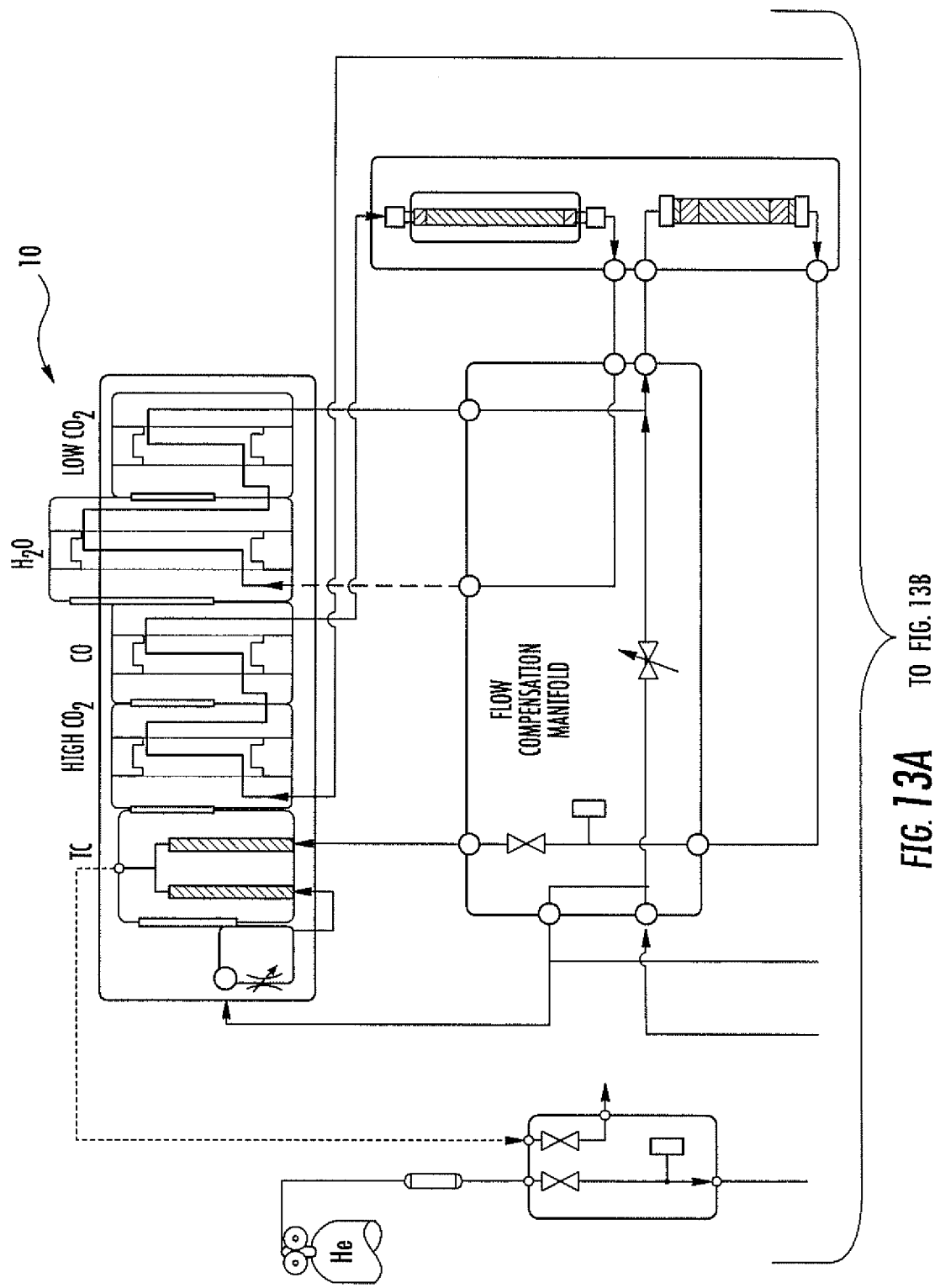
FIGS. 13A and 13B are a flow diagram of an analytical instrument embodying the present invention.
Figure 13B:
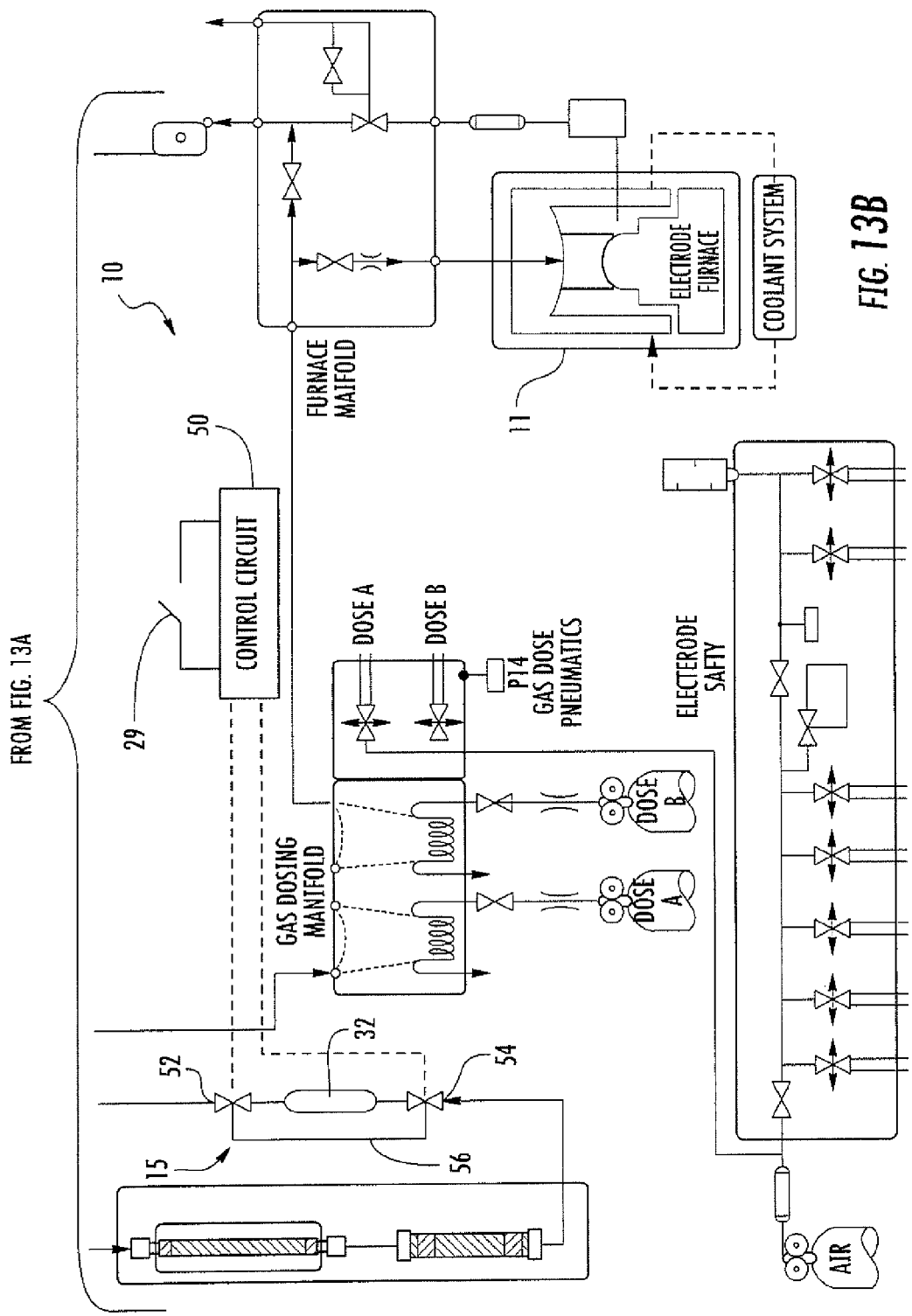

Referring initially to FIGS. 1, 2, 13A and 13B, there is shown an instrument 10 for the analysis of elements, such as nitrogen, oxygen, hydrogen, or the like, utilizing an electrode resistance furnace. The instrument 10 can be a Model TCH-600, commercially available from Leco Corporation of St. Joseph, Mich. Instrument 10 includes an electrode furnace 11 (FIG. 13B) employing carbon crucibles holding a sample to be fused or heated. The resultant gases are analyzed in a conventional manner utilizing an inert carrier gas, such as helium, with a flow path for the instrument as illustrated in FIGS. 13A and 13B. Although the helium used is typically a high quality laboratory grade, it still may contain some oxygen and moisture which interferes with the accurate analysis of the sample. Accordingly, the instrument 10 includes a final or finish scrubber 15 (FIGS. 2 and 13B), which is located closely adjacent the input to the furnace and in the carrier gas flow path. In the past, these scrubbers (also known as OMI (oxygen moisture indicator)) have been mounted to the instrument by threaded fittings which require tools for the removal and replacement of the final scrubber, as well as significant down time for the instrument. Also, the flow of carrier gas is forced to bypass the furnace during the replacement period of time, which can disrupt the purged gas pathway.

Figure 1:
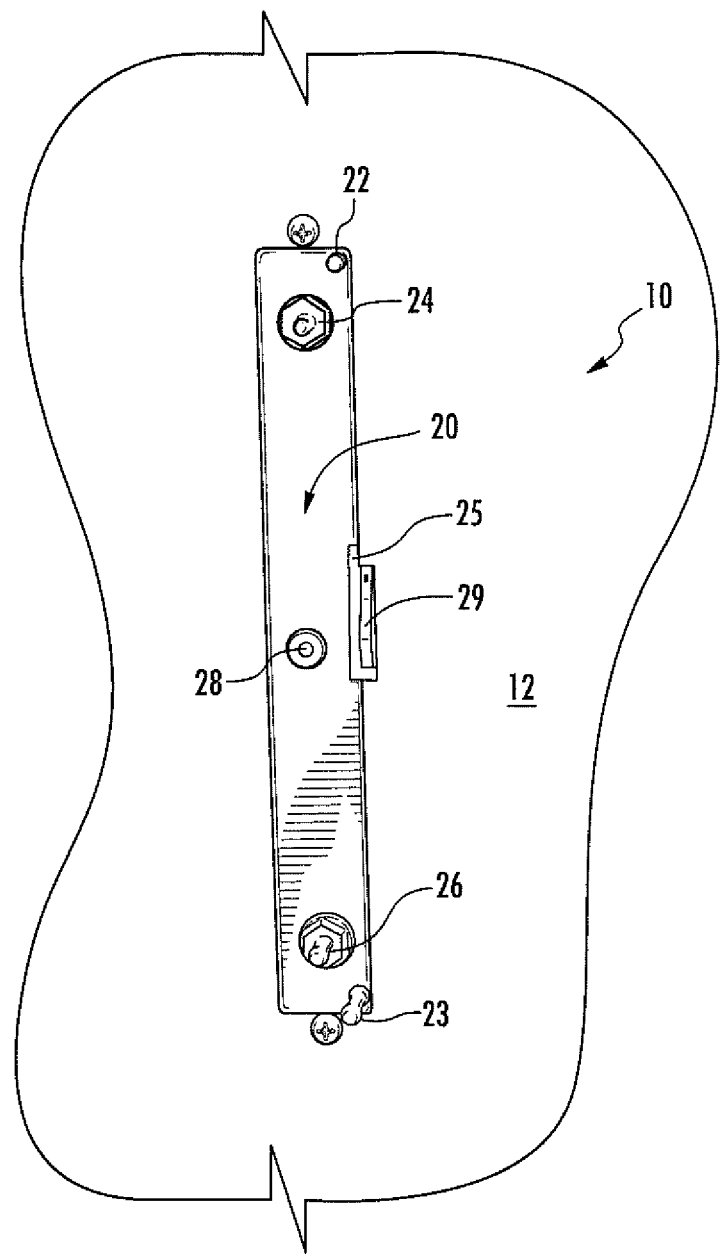
FIG. 1 is a fragmentary front elevation view of an analyzer showing the front of a manifold for receiving a removable final scrubber housing.
Figure 6:
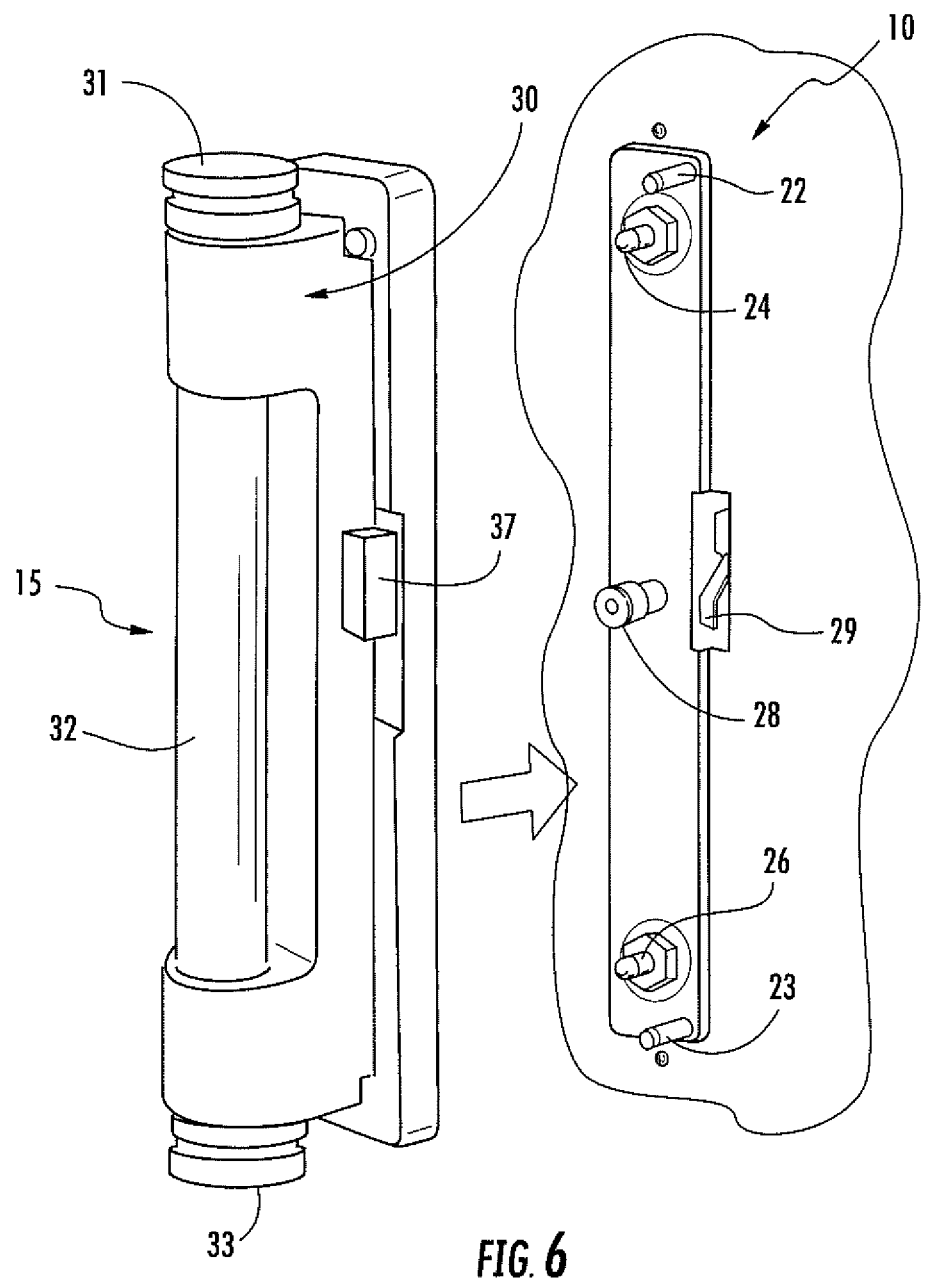
FIG. 6 is a perspective view illustrating the mounting and removal of the housing from the manifold.

The system of the present invention provides a manifold assembly 20 mounted on the front wall 12 of the instrument, as illustrated in FIG. 1, for removably receiving the housing assembly 30 of the final scrubber 15, as illustrated in FIGS. 2, 6, 10, and 11. The housing 30 includes a filter cartridge 32, such as available from the Sigma-Aldrich Company, Model Supelco 2-3906, which is a lithium-based reagent for removing oxygen and moisture from a carrier gas stream. The cartridge is held within the housing by an upper and lower end caps 31 and 33, respectively, which allow the easy and fast replacement of the cartridge 32 once housing 30 is removed from the manifold 20 of instrument 10. The user of the instrument 10 may have a backup housing 30 with a new cartridge 32 to facilitate the quick replacement of the final scrubber or may remove the housing 30, replace the filter cartridge 32 while it is removed, and then reconnect the housing 30 to the manifold 20 (as illustrated in FIG. 6).

Figure 3:
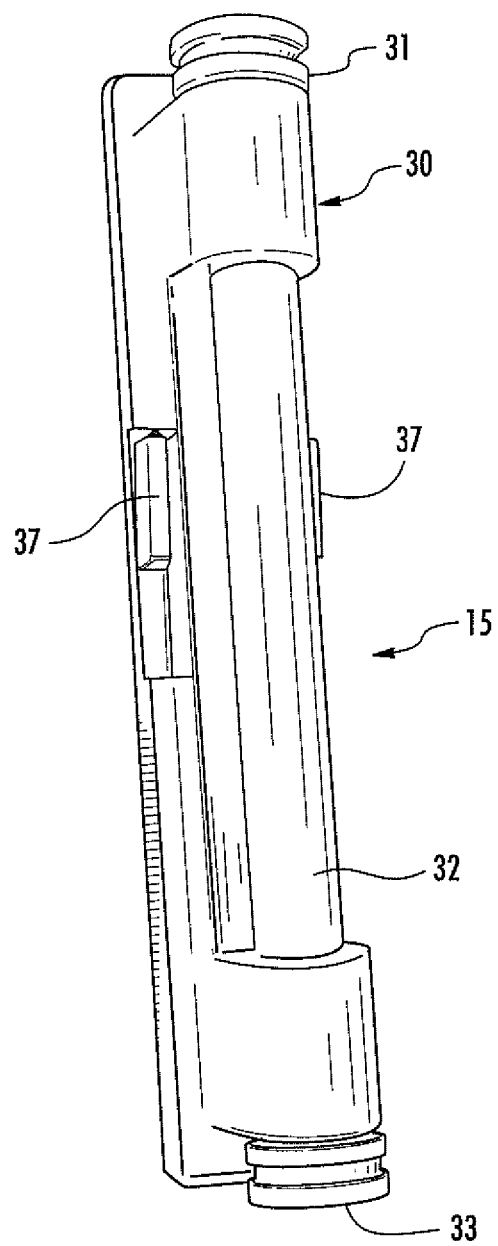
FIG. 3 is a front perspective view of the housing and filter tube of the final scrubber.

The housing and manifold cooperate with one another to provide both a locked mechanical connection as well as a sealed gas stream connection. The manifold 20 includes input and output three-way valves 52 and 54 (FIGS. 13A and 13B), which automatically bypass the final scrubber 15 when removed from the manifold, as seen in FIGS. 1, 3 and 6. As illustrated in FIG. 13B, the system provides a bypass flow path 56 for the inert gas stream which can continue to flow through the furnace keeping it purged of any contamination. The three-way valves 52, 54 also can be actuated to allow segmented leak detection of the gas flow path in the instrument. The manifold 20 includes a pair of alignment pins 22 and 23 extending outwardly at the upper and lower corners, as seen in FIG. 1. These pins mate with corresponding apertures 41 and 43 (FIGS. 4 and 5) extending through the back plate 40 of final scrubber housing 30. These pins 22 and 23 also act to prevent the user from placing the housing 30 onto the manifold 20 without first securing the end caps 33 into the proper position as described below.

Figure 7:
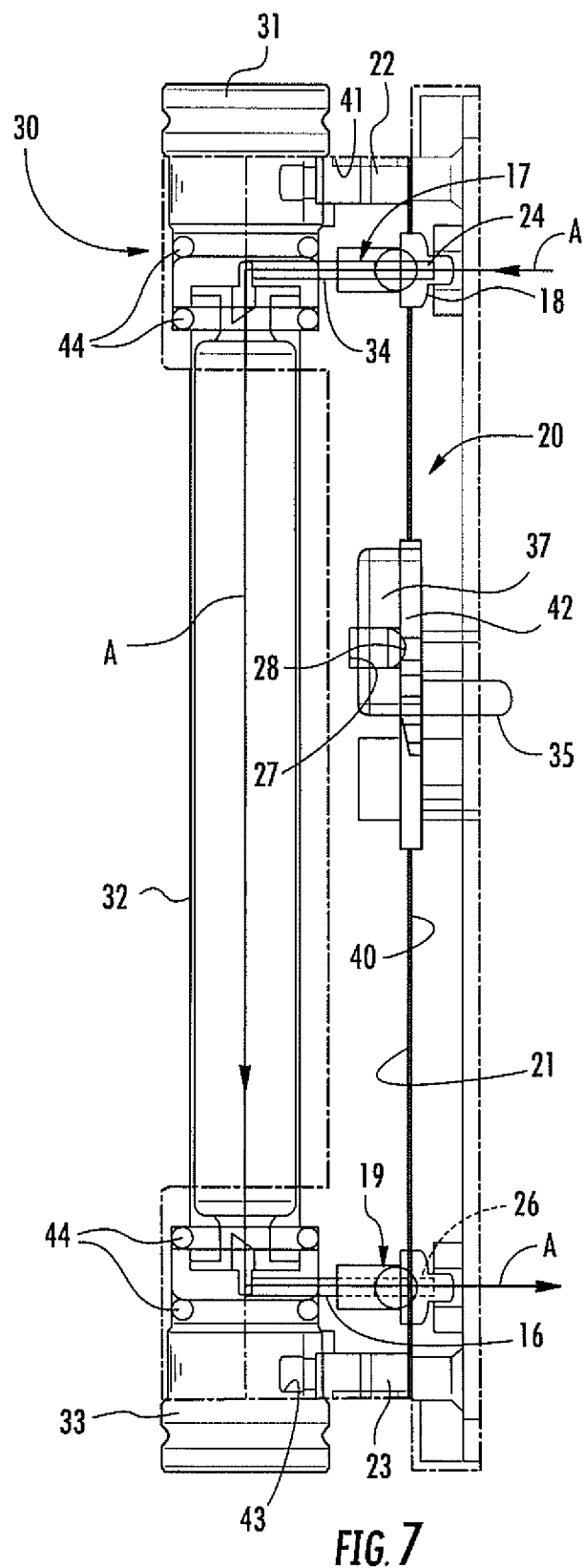
FIG. 7 is a vertical cross-sectional view of the manifold and housing assembly engaged for the use of the final scrubber.
Figure 7A:
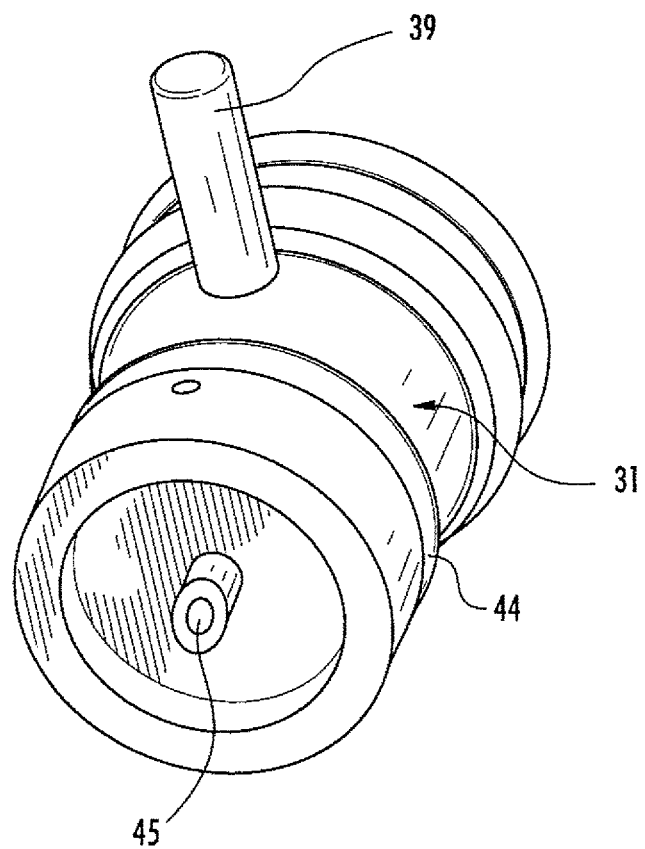
FIGS. 7A-7D are perspective sequential views of the mounting of one of the end caps to the housing.
Figure 7B:
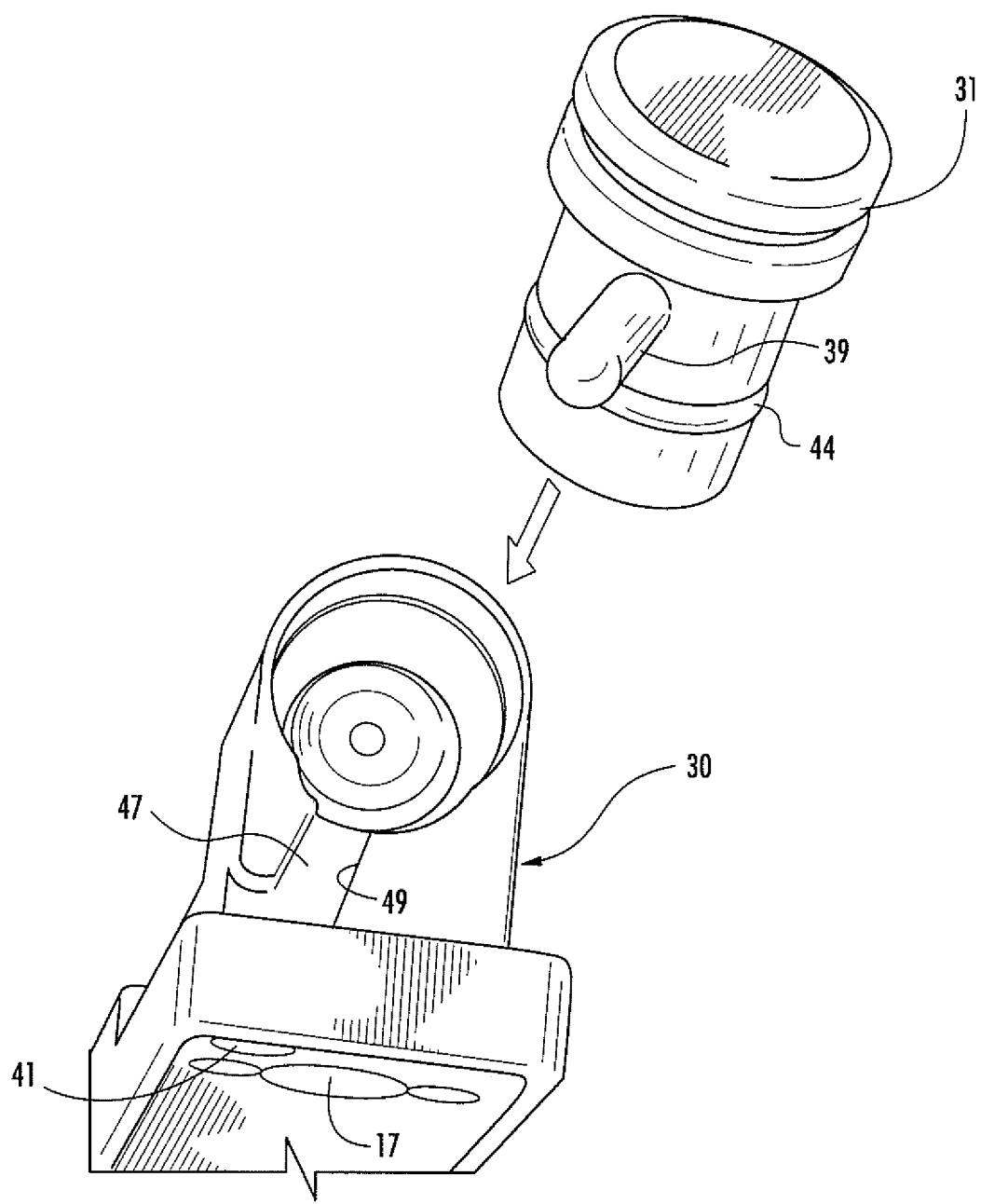
Figure 7C:
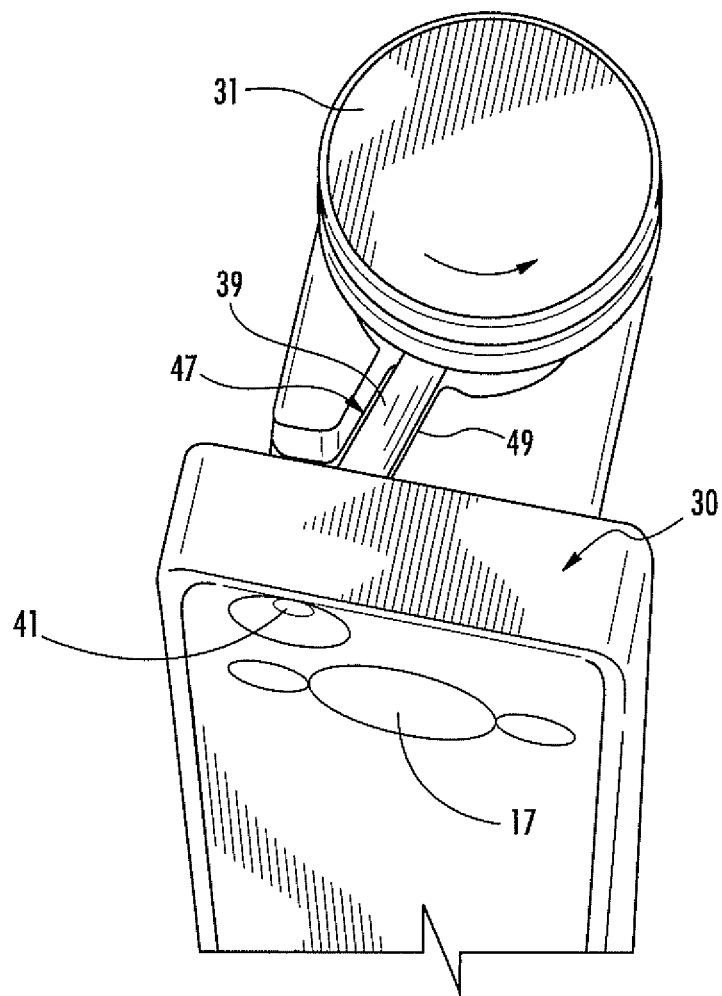
Figure 7D:
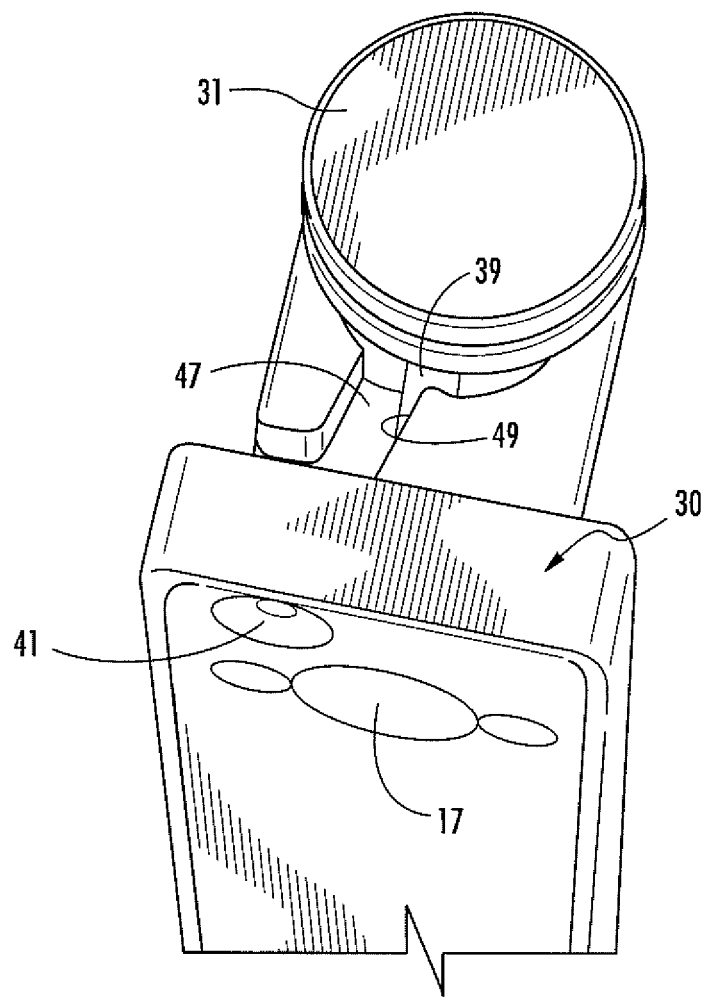
Figure 8:
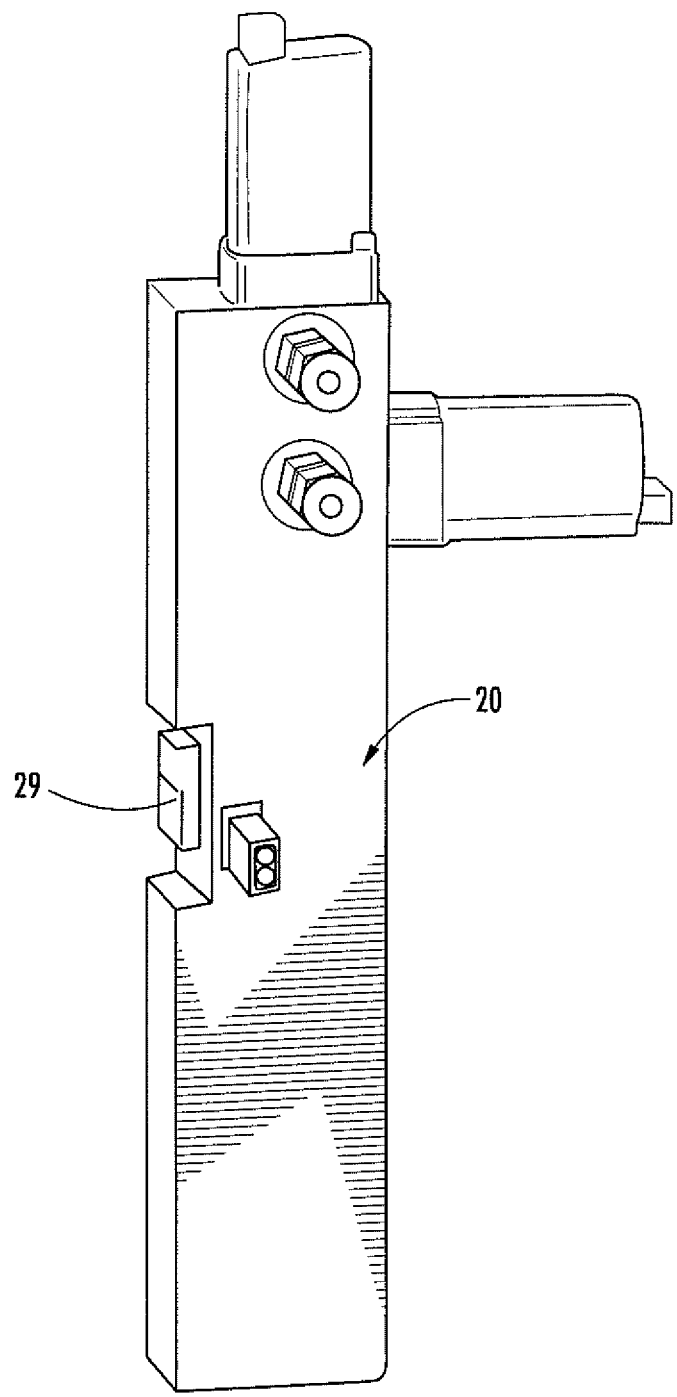
FIG. 8 is a rear perspective view of the manifold seen in FIGS. 1 and 7.
Figure 9:
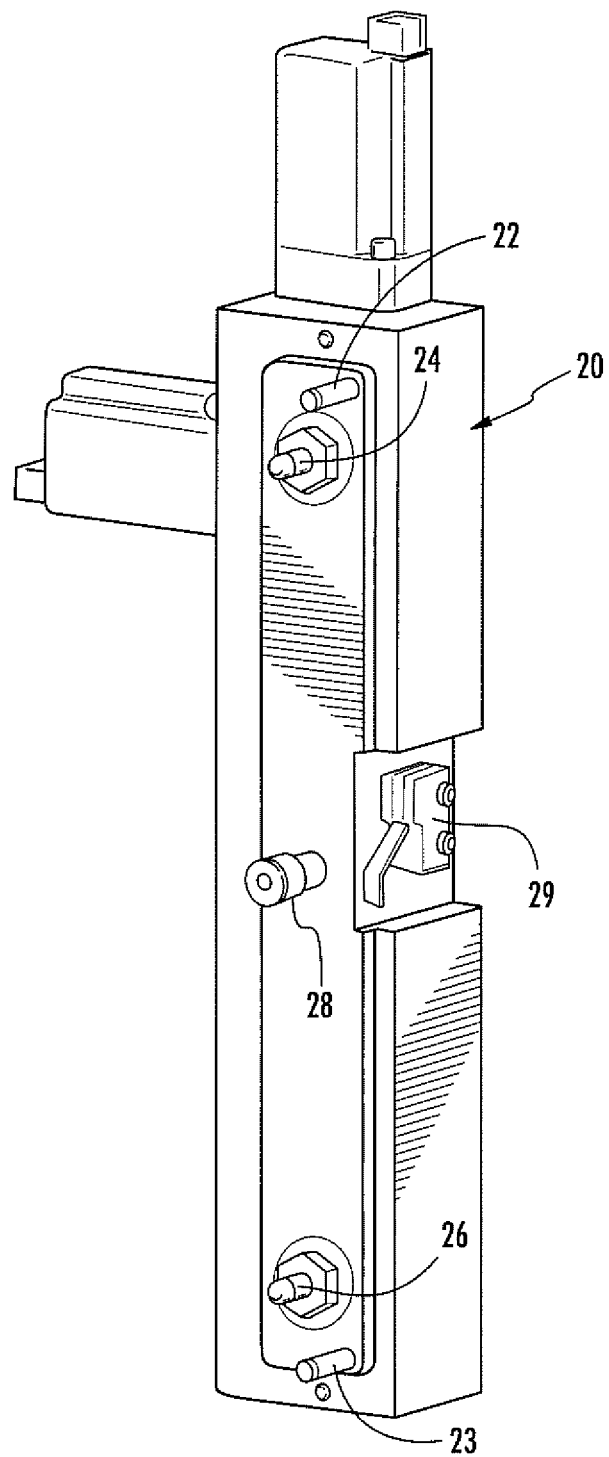
FIG. 9 is a front perspective view of the manifold seen in FIG. 8.

The end caps 31, 33 of the housing 30 are used to pierce the foil seals of the final scrubber cartridge 32 and include O-ring seals 44 to provide a sealed connection to cartridge 32. The end caps 31 and 33 also have lock pins 39 that lock the end caps in place on the housing 30 (FIGS. 7A-7D). As the end caps pierce the foil with a piercing tube 45 (FIG. 7A), pin 39 enters slot 47 (FIG. 7C). The user then rotates the end caps 31, 33 to engage under a lip 49 adjacent slot 47 as seen in FIG. 7D to lock caps 31, 33 in place. If the lock pins 39 are not properly rotated and engaged, they will encounter the matching alignment pins 22 or 23 on the manifold 20 (FIG. 7C) extending through apertures 41 and 43 and prevent installation of the housing 30 to the manifold 20. This feature is designed to ensure that the final scrubber cartridge 32 is not placed on the manifold 20 without the lock pins 39 and end caps 31, 33 properly sealably engaged. This feature also prevents the sensor switch 29 from becoming activated, pressurizing the final scrubber cartridge 32 causing the end caps 31, 33 to inadvertently pop off if not properly secured.

The housing 30 also includes spring-loaded valves 17 and 19 (FIG. 7) which seal the cartridge 32 when removed from manifold 20. This prevents contamination from entering the cartridge 32 prior to installation of the final scrubber 15 to the instrument. The projecting gas fittings 24 and 26 mechanically actuate the spring-loaded valves 17, 19, respectively, to open them when the final scrubber is installed on the manifold.

Figure 2:
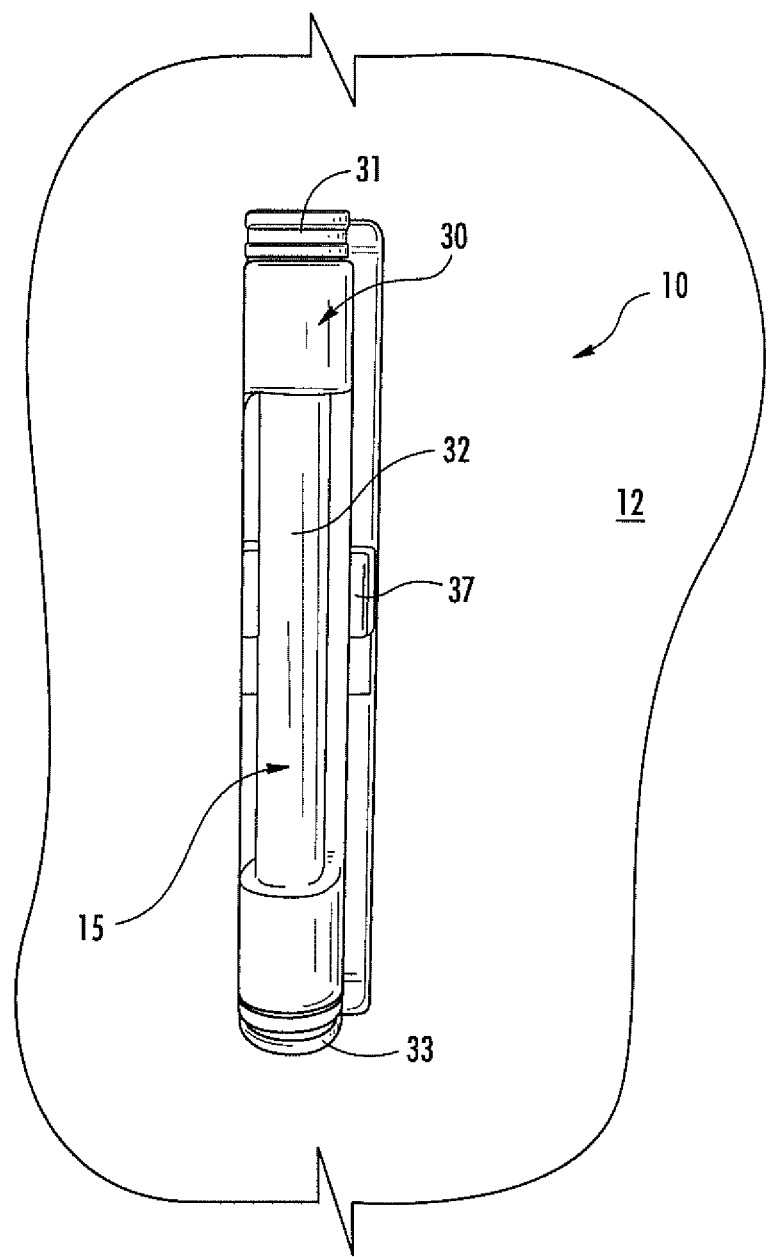
FIG. 2 is a front elevation view as seen in FIG. 1 shown with the final scrubber mounted in place.
Figure 10:
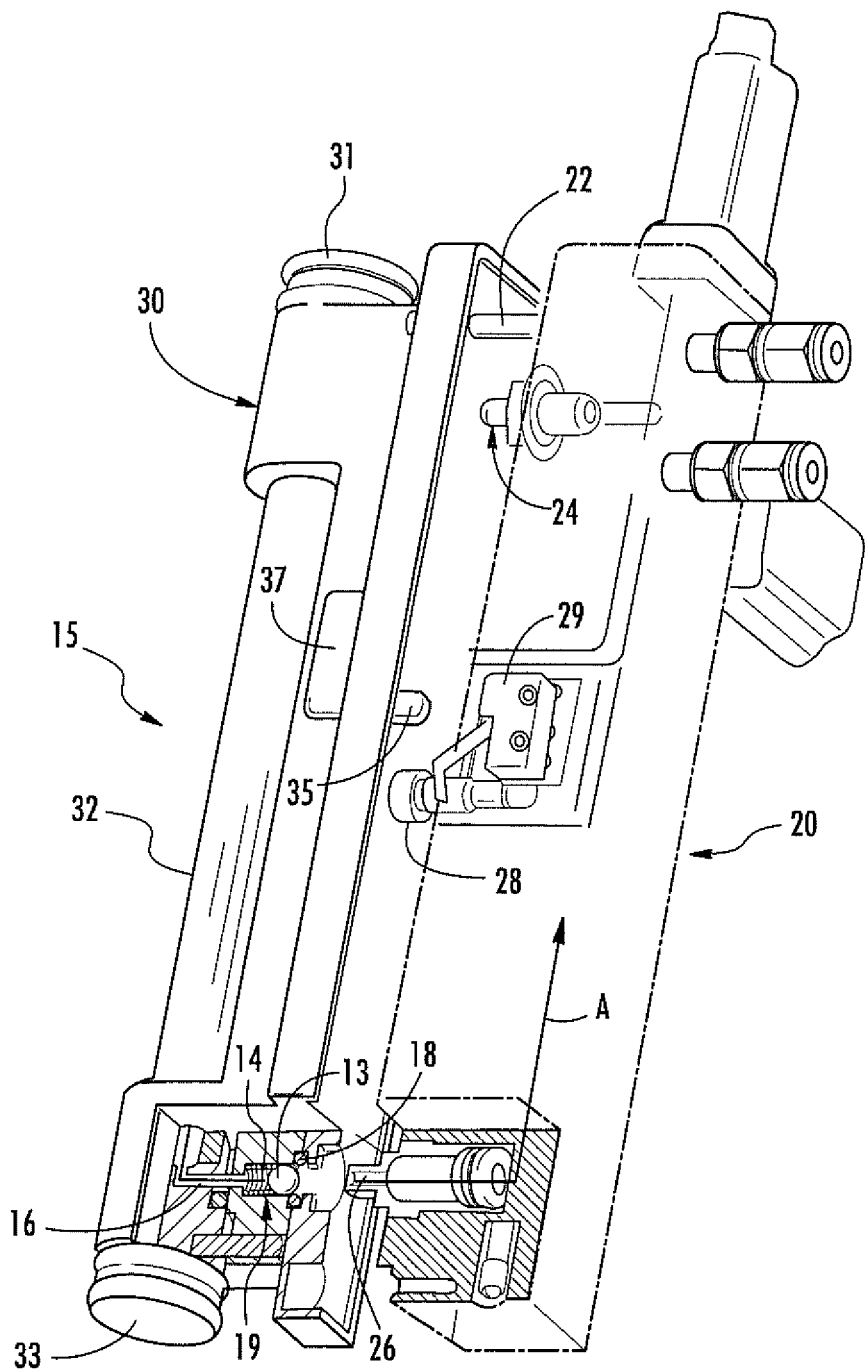
FIG. 10 is a right side perspective view, partly in cross section and partly exploded, of the housing and manifold of the present invention.
Figure 11:
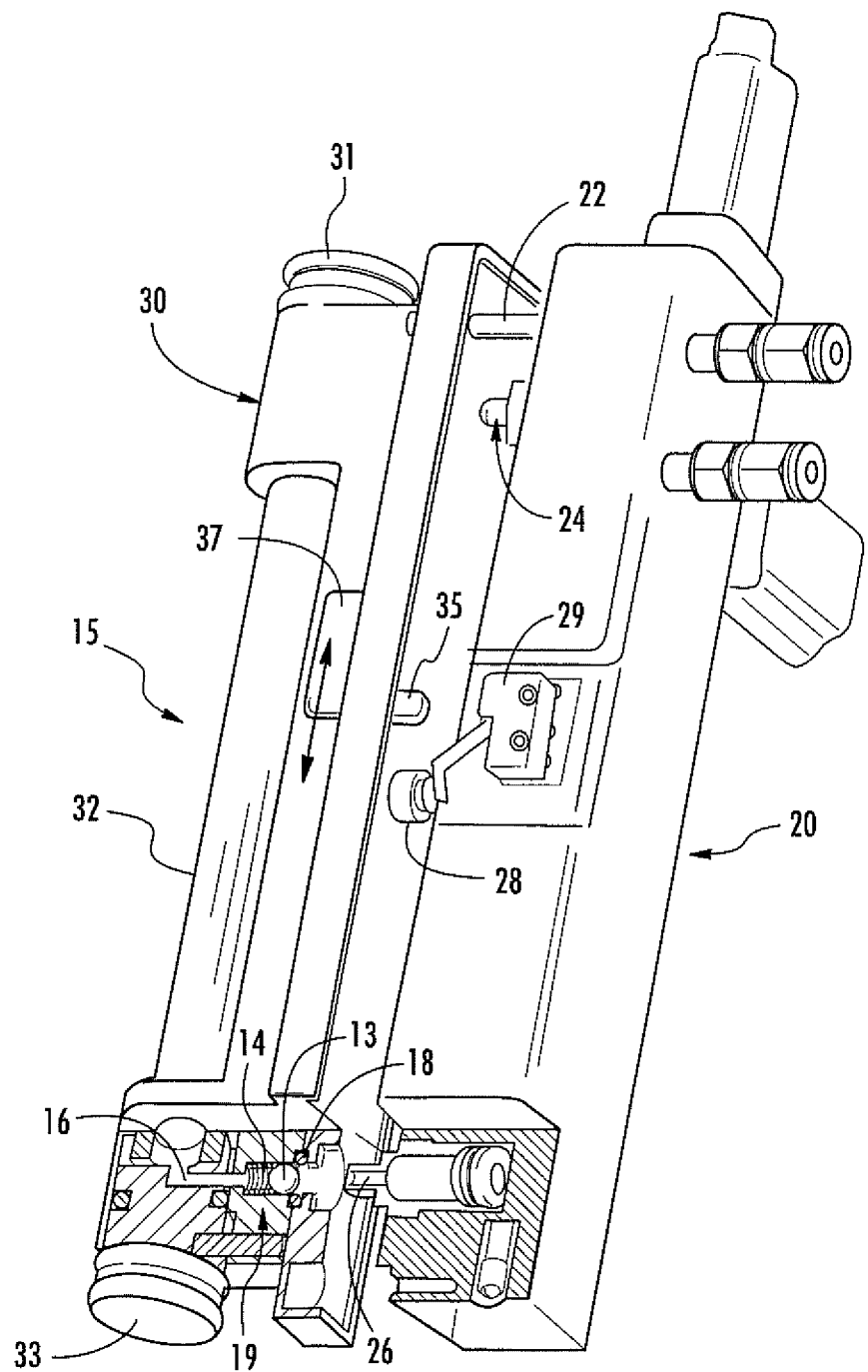
FIG. 11 is a right side perspective view, partly in cross section and partly exploded, of the housing and manifold of the present invention.
Figure 12:
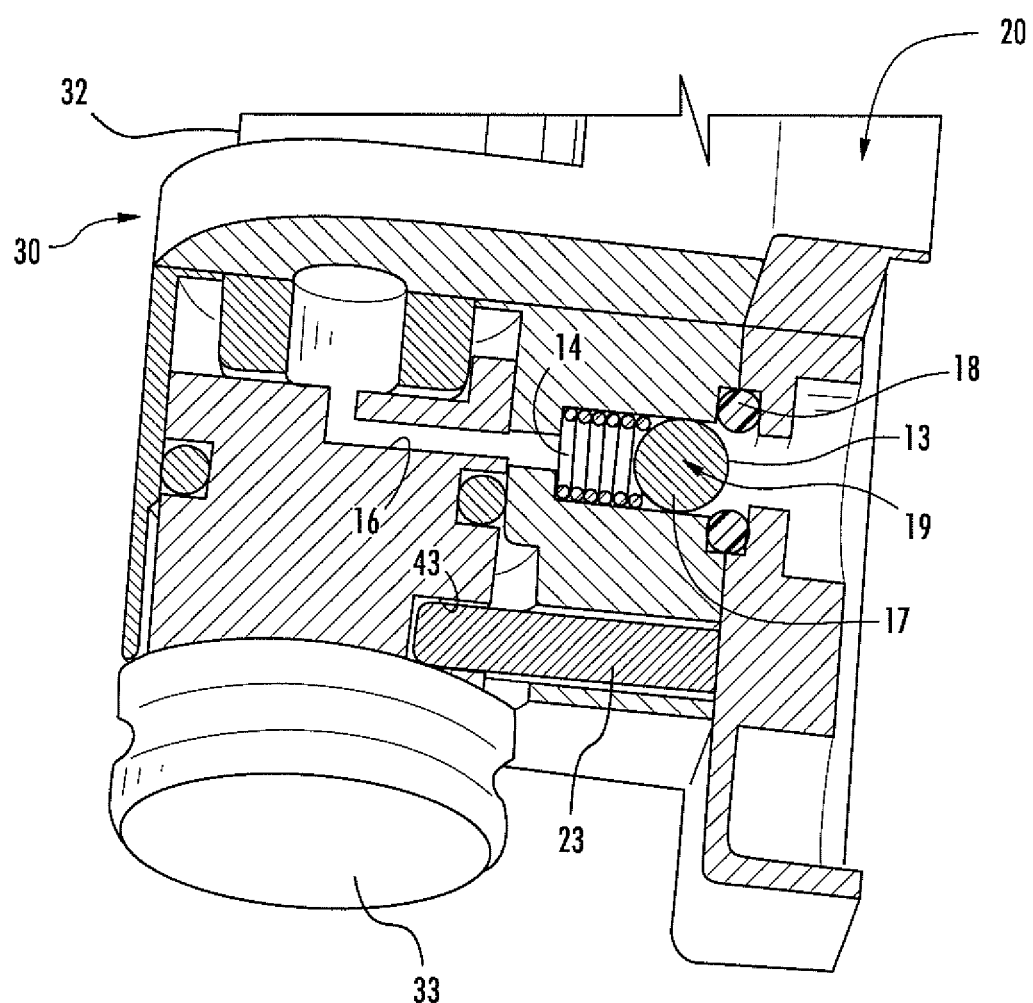
FIG. 12 is an enlarged fragmentary perspective cross-sectional view of the gas connection at the lower end of the housing and manifold.

The lower spring-loaded valve 19 includes, as best seen in FIG. 12, a ball 13 and a backing compression spring 14, which urges ball 13 into sealed engagement with O-ring seal 18. The projecting gas fitting 26 (FIGS. 10 and 11) of manifold 20 pushes ball 13 away from seal 18, opening the gas flow path 16 in end cap 33, and through filter cartridge 32. The upper valve 17 is constructed similarly to valve 19. Once housing 30 is mounted to manifold 20 as seen in FIG. 2, a sealed gas connection is made at the upper fitting 24 as well as at a similarly valved lower fitting 26 providing a gas flow path as indicated by arrow A in FIG. 7, through the mating gas valves 17, 19 in housing 30. Thus, when housing 30 is installed, as seen in FIGS. 2, 7 and 10, on the instrument, the gas flow path extends from fitting 24 through valve 17 and as flow path 34 through the filter cartridge 32 and exits the assembly through valve 19 and into fitting 26 to the instrument in the flow path, also illustrated in FIGS. 13A and 13B. The connections of the instrument to the fittings 24 and 26 at the back of the manifold 20 are substantially conventional.

Figure 4:
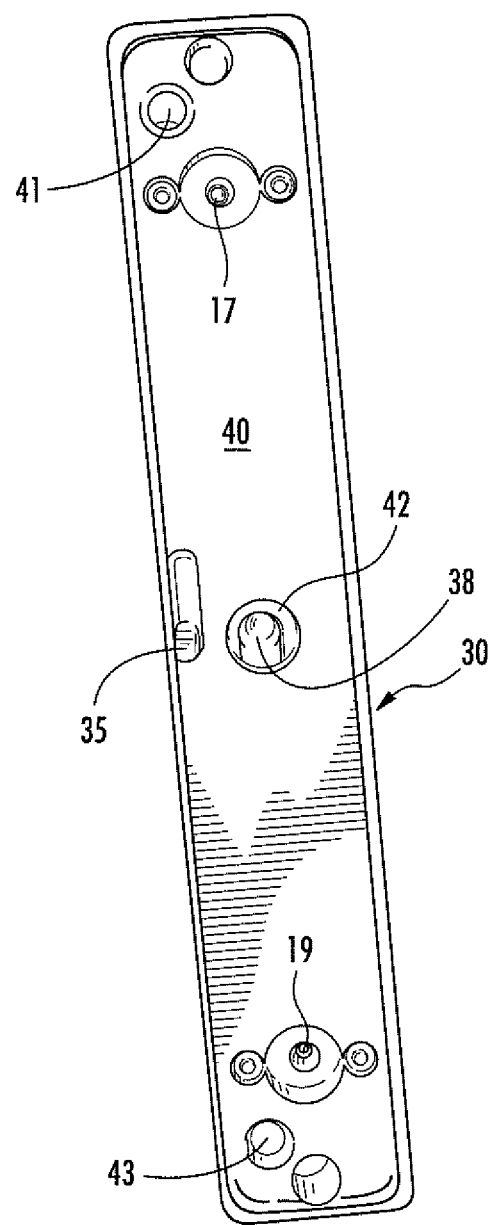
FIG. 4 is a rear elevation view of the housing shown in FIG. 3, with the latch in a latched position.
Figure 5:
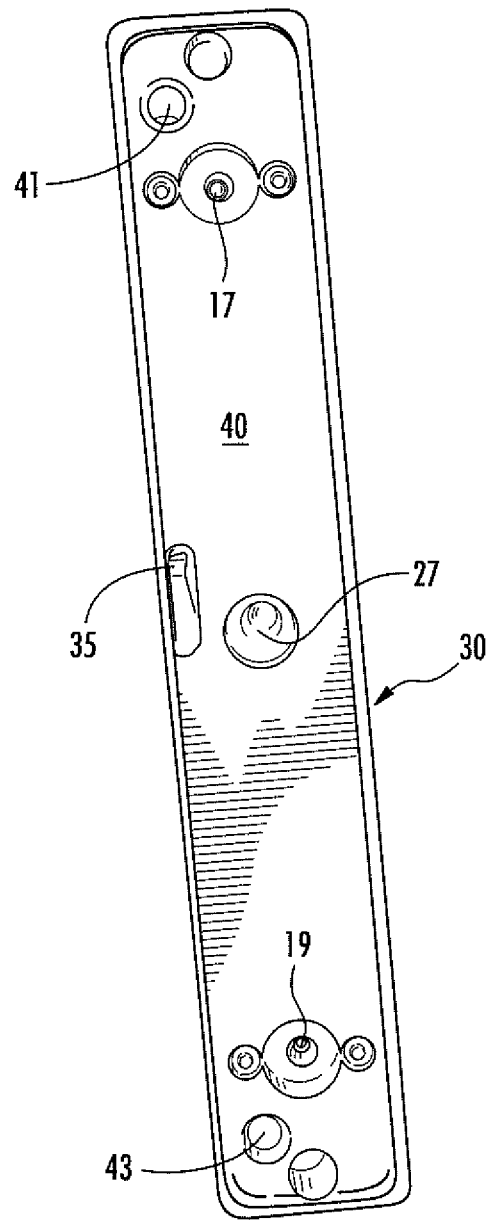
FIG. 5 is a rear elevation view of the housing shown in FIG. 4, with the latch in an unlatched position.

The manifold 20 includes a slot 25 along one edge, as illustrated in FIG. 1, for receiving a sliding actuator 35 (FIGS. 4, 5, and 7) on the housing 30 which is actuated by an operator accessible handle 37 (FIGS. 2 and 7). The latch includes a sliding plate 42 in a slot behind the back plate 40. Plate 42 includes a U-shaped slot 38, as seen in FIG. 4. The edges of the U-shaped slot engages and positively locks the housing 30 to a catch, which is the head of a post 28 centered on the faceplate 21 of manifold 20 when in the mounted position (FIG. 2) with the latch in a locked position shown in FIG. 4. An aperture 27 (FIG. 5) in housing 30 provides clearance for the head of post 28, such that the edges of slot 38 can engage the post 28. With latch handle 37 raised, moving locking plate slot 38 and actuator 35 upwardly as illustrated in FIG. 5, the latch and catch disengage, and the housing 30 can be removed from the manifold in a direction opposite the arrow illustrated in FIG. 6.

The manifold 20 also includes an electrical contact switch 29 adjacent slot 25 which is engaged by the sliding actuator 35 of housing 30 when mounted on the instrument 10 to provide a signal to a control circuit 50 (FIG. 13B) to actuate the three-way solenoid or pneumatic valves 52 and 54, via the electrical connection illustrated in dashed lines, to automatically bypass the final scrubber 15 and provide a bypass flow path 56 through the furnace for the gas stream when housing 30 is removed. With this system, the final scrubber can be removed and replaced quickly without the use of tools while the gas continues to flow though the furnace without interruption of the purging gas flow path through the instrument's furnace. When not installed on the manifold, the spring-loaded valves of the housing 30 seal the final scrubber. Also, the valves 52, 54 can be closed to allow for segmented leak detection of the instruments gas flow path.

It will become apparent to those skilled in the art that various modifications to the preferred embodiment of the invention as described herein can be made without departing from the spirit or scope of the invention as defined by the appended claims.

The invention claimed is:

1. A system for changing a filter cartridge in an analyzer comprising:

a fluid flow path including a manifold with input and output fluid fittings and at least one valve coupled to one of said input and output fittings; and a housing for a filter cartridge, said housing including housing fluid conduits which align with and couple to associated ones of said input and output fluid fittings of said manifold, wherein said manifold includes a sensor switch which is actuated when said housing is positioned on or removed from said manifold; and wherein said manifold further includes a three-way valve coupled to said input fitting and a three-way valve coupled to said output fitting and wherein said system includes a control circuit coupled to said sensor switch and to said three-way valves for actuating said three-way valves when said housing is positioned on or removed from said manifold, such that, when said housing is removed from said manifold for the replacement of a filter cartridge mounted to said housing, said three-way valves shut off the flow path to said input and output fittings.

2. The system as defined in claim 1 and further including a bypass flow path coupled to said three-way valves to bypass said housing when removed from said manifold.

3. A system for changing a final scrubber in an analytical instrument comprising:
   a gas flow path for a carrier gas, said path including a manifold with input and output gas fittings; and
   a housing including a filter cartridge, said housing further including housing input and output spring-loaded valves which align with and couple to associated ones of said input and output gas fittings of said manifold, said housing interacting with said manifold to actuate said spring-loaded valves, such that, when said housing is not installed on said manifold, said filter cartridge is sealed, wherein said manifold includes a three-way valve coupled to said input fitting and a three-way valve coupled to said output fitting and a sensor switch which is actuated when said housing is positioned on or removed from said manifold, and wherein said system includes a control circuit coupled to said sensor switch and to said three-way valves for actuating said three-way valves when said housing is positioned on or removed from said manifold.

4. The system as defined in claim 3 and further including a bypass flow path coupled to said three-way valves to bypass said housing when removed from said manifold.

5. The system as defined in claim 4 wherein said manifold includes one of a latch and catch and said housing includes the other of a latch and catch such that said housing can be releasably locked on to said manifold.

6. A system for changing a filter cartridge in an analyzer furnace for the analysis of a sample, said system comprising:
   a manifold for a carrier gas, said manifold having input and output gas fittings;
   a housing for a filter cartridge, said housing including housing fittings which align with and couple to associated ones of said input and output gas fittings of said manifold such that said housing can be removably attached to said manifold for the replacement of a filter cartridge mounted to said housing;
   a sensor switch for detecting the presence of said housing on said manifold; and
   wherein said manifold further includes a three-way valve coupled to said input fitting and a three-way valve coupled to said output fitting and wherein said system includes a control coupled to said sensor switch and to said valves for actuating said valves when said housing is positioned on or removed from said manifold.

7. The system as defined in claim 6 wherein said manifold includes one of a latch and catch and said housing includes the other of a latch and catch such that said housing can be releasably locked on to said manifold.

8. The system as defined in claim 7 and further including a bypass flow path coupled to said three-way valves to bypass said housing when removed from said manifold.

9. The system as defined in claim 6 wherein said manifold includes at least one of an alignment pin or aperture and said housing includes the other of at least one of an alignment pin or aperture for aligning said housing to said manifold as it is mounted thereto.

10. The system as defined in claim 6 wherein said housing fittings include an input fitting and an output fitting, each including a spring-loaded valve which are actuated to open when said housing is installed on said manifold.

11. The system as defined in claim 10 wherein said spring-loaded valves each include a ball and seal and wherein said input and output gas fittings of said manifold engage said balls to force them away from said seals to open the flow path through said filter cartridge when said housing is installed on said manifold.

\* \* \* \* \*